United States Patent [19]

Colquhoun et al.

[11] Patent Number: 4,599,452

[45] Date of Patent: Jul. 8, 1986

[54] CHEMICAL PROCESS

[75] Inventors: Howard M. Colquhoun, Knutsford; Alan G. Breeze, Northwich, both of England

[73] Assignee: Imperial Chemical Industries PLC, London, England

[21] Appl. No.: 616,894

[22] Filed: Jun. 4, 1984

[30] Foreign Application Priority Data

Jun. 7, 1983 [GB] United Kingdom ............... 8315612

[51] Int. Cl.$^4$ ............................................. C07C 45/46
[52] U.S. Cl. ..................................... 568/319; 568/322
[58] Field of Search .................... 568/319, 322; 560/66

[56] References Cited

U.S. PATENT DOCUMENTS

| | | | |
|---|---|---|---|
| 2,728,747 | 12/1955 | Aelong et al. | 560/66 |
| 2,763,691 | 9/1956 | Kowles | 568/319 |
| 3,073,866 | 1/1963 | Stanley | 568/322 |
| 3,160,665 | 12/1964 | Siegrest et al. | 568/319 |
| 3,548,005 | 12/1970 | Milionis et al. | 568/322 |
| 3,549,593 | 12/1970 | Takekoshi | 560/66 |
| 3,759,870 | 9/1973 | Economy et al. | 560/66 |
| 4,453,010 | 6/1984 | Staniland | 568/322 |

FOREIGN PATENT DOCUMENTS 0069598  1/1983  European Pat. Off. ............ 568/322

OTHER PUBLICATIONS

Stille, Condensation Monomers (1972), John Wiley & Sons, pp. 620–623.
Hill, Jo. Am. Chem. Soc., vol. 54, pp. 4105–4106 (1932).

Primary Examiner—James H. Reamer
Attorney, Agent, or Firm—Cushman, Darby & Cushman

[57] ABSTRACT

Preparation of para-substituted 4-hydroxybenzophenones by reacting appropriately substituted aromatic compound with poly(4-oxybenzoyl) in the presence of an acid catalyst. The reaction with the appropriately substituted aromatic compound, for example fluorobenzene, is effected in the presence of an acid catalyst such as a strong proton acid or a Lewis Acid or a mixture thereof.

11 Claims, No Drawings

CHEMICAL PROCESS

This invention relates to a chemical process and more particularly to a method for the preparation of 4-hydroxybenzophenones.

A number of substituted diaryl ketones, for example 4-fluoro-4'-hydroxybenzophenone, are useful as precursors of poly(arylene ether ketones). Several methods have been proposed for the preparation of these ketones but none has proved to be entirely satisfactory.

Thus, it is known to make 4-fluoro-4'-hydroxybenzophenone by reacting phenol with 4-fluorobenzoic acid in anhydrous hydrogen fluoride with or without the addition of boron trifluoride. The reaction provides the desired product in high yield and good selectivity but has a number of disadvantages which make it unattractive as a basis for an industrial process. First, 4-fluorobenzoic acid is a very costly starting material. Second, water, formed as a by-product of the reaction produces, in conjunction with the hydrogen fluoride, an extremely corrosive reaction mixture which severely limits the plant materials that may be employed, a situation which is further aggravated when boron trifluoride is present. Third, because of the water produced, the hydrogen fluoride has to be dehydrated before being recycled.

It is also known to make 4-fluoro-4'-hydroxybenzophenone by reacting 4-hydroxybenzoic acid with fluorobenzene in anhydrous hydrogen fluoride in the presence of boron trifluoride. This method avoids using the expensive fluorobenzoic acid but still suffers from the disadvantages mentioned above associated with the formation of water as by-product.

It has now been found that 4-hydroxybenzophenones may be prepared in excellent yield by reacting poly(4-oxybenzoyl) with appropriately substituted aromatic hydrocarbons in the presence of an acid catalyst. This method, which makes use of commercially available or readily preparable starting materials, has the very important advantage over the above mentioned prior art methods that water is not a by-product of the reaction. Corrosion problems when using hydrogen fluoride as solvent/catalyst are therefore minimised and recycling of the solvent/catalyst is simplified.

Thus, in accordance with the invention, a process is provided for the preparation of a 4-hydroxybenzophenone having the formula:

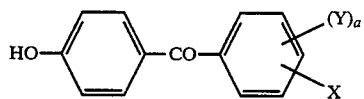

which process comprises reacting an aromatic compound of the formula:

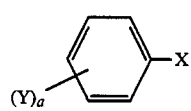

with poly (4-oxybenzoyl) in the presence of an effective amount of an acid catalyst, wherein X is a hydrogen or a substituent which is not strongly electron-attracting;

Y is a substituent which is not strongly electron attracting; and a is zero or an integer of 1 to 4;

the remaining substituents being hydrogen atoms, and the overall effect of X and the substituents Y is not sufficient to deactivate the aromatic compound to such an extent that substitution occurs only with difficulty.

If the group X is not hydrogen, it is a substituent which is not strongly electron-attracting, and may be an electron-donating substituent, for example alkyl alkoxy or aryloxy, a substantially neutral substituent, for example aryl, or a mildly electron-attracting substituent for example halogen. In this connection, a strongly electron-attracting substituent is to be regarded as one which is more strongly electron-attracting than chlorine, for example cyano, nitro, alkylcarbonyl, alkoxycarbonyl or alkylsulphonyl. Persons skilled in the art will have no difficulty in identifying substituents which are not strongly electron-attracting when attached to an aromatic nucleus but a useful indication of the electron-donating or attracting properties of substituents may be obtained from their Hammett $\sigma$ constants which have been displayed and discussed by Clark and Perrin in Quarterly Reviews, Vol 18, 1964, pp 295–320. Substituents having a $\sigma$ constant for para-substitution of more than 0.4 tend to give a slow reaction and hence it is preferred to use substituents having a $\sigma$ constant of less than 0.4.

Thus, aromatic compounds which may be reacted with poly(4-oxybenzoyl) in accordance with the invention include benzene, alkylbenzenes for example toluene, alkoxybenzenes for example anisole, arylbenzenes for example biphenyl and 4-fluorobiphenyl, aryloxybenzenes for example diphenyl ether and 4-fluorodiphenyl ether and halogenobenzenes for example fluorobenzene, chlorobenzene and bromobenzene. In addition to the substituent X, the aromatic compound may carry one or more other substituents Y provided that the overall effect of all of the substituents (including X) is not deactivation of the aromatic compound to such an extent that reaction occurs only with difficulty. If the group Y is an even mildly electron-withdrawing group, for example halogen, it is preferred that there are not more than two Y groups, and especially not more than one. The group Y may be the same as, or different from, the group X. Thus other aromatic compounds which may be used include mxylene, naphthalene and substituted naphthalenes free from strongly electron-attracting substituents. It is preferred that the aromatic compound is unsubstituted in the para-position to the X substituent.

The poly(4-oxybenzoyl) used in the process of the invention is a polyester having the general formula:

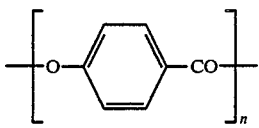

where n has a value representing the degree of polymerisation. The value of n may be in the range from 2 to 1000 and is typically in the range 5 to 200. Relatively high molecular weight material (n having a value of the order of 100) is available commercially under the trade mark "Ekonol" and may be used in the method of the invention with excellent results. Lower molecular weight material (n having a value of less than 10) is somewhat more soluble in aromatic solvents and allows a wider range of reaction media to be employed, for example 1,2-dichlorobenzene and 1,2,4-trichlorobenzene, although it should be noted that 1,2-dichlorobenzene has a low reactivity in the process of the present invention and is suitable for use as an inert solvent only when a more reactive compound, such as diphenyl ether, is used as the aromatic compound. Suitable low molecular weight material may be obtained, for example, by reacting 4-hydroxybenzoic acid with trifluoroacetic anhydride in methylene chloride.

Acid catalysts which may be used in the process of the invention include, in particular, strong proton acids and Lewis acids and mixtures thereof, especially mixtures of strong proton acids or mixtures of a strong proton acid and a Lewis acid.

As examples of suitable Lewis acids which may be used, there may be mentioned boron trifluoride, titanium tetrafluoride, the pentafluorides of tantalum, niobium, phosphorus, arsenic and antimony and the corresponding chlorides and bromides and aluminium chloride. Suitable proton acids include hydrogen fluoride, trifluoromethanesulphonic acid, methanesulphonic acid, perchloric acid and fluorosulphonic acid. Useful mixtures of acids include mixtures of hydrogen fluoride with boron trifluoride, antimony pentafluoride, tantalum pentafluoride or trifluoromethanesulphonic acid.

Preferred catalysts include hydrogen fluoride, hydrogen fluoride/boron trifluoride mixtures and trifluoromethanesulphonic acid with high molecular weight polymers, but aluminium chloride can be used with polymers of relatively low molecular weight, for example those in which the value of n is 5 to 20.

Reaction between the aromatic compound and the poly(4-oxybenzoyl) may be performed at temperatures in the range 20° to 150° C. The most suitable temperature and duration of reaction varies to some extent according to the particular aromatic compound and acid catalyst being employed and is also influenced by the polyester molecular weight. In general, temperatures in the range 60° to 100° C. are preferred, the reaction time suitably being between 2 and 24 hours. Pressures may be atmospheric or higher.

The reaction may be conveniently performed using at least one mole of aromatic compound for each molecular equivalent (that is repeat unit) of oxybenzoyl units. Similarly, the strong proton acid and Lewis acid are preferably used in amounts of at least one equivalent for each molecular equivalent of oxybenzoyl units.

If desired, the reaction may be carried out in an inert solvent such as 1,2,4-trichlorobenzene nitrobenzene or sulphur dioxide but in some cases it may be more convenient to employ an excess of the aromatic compound as reaction medium or an excess of a strong proton acid, for example hydrogen fluoride or trifluoromethanesulphonic acid. However, it is possible to use mixtures as the reaction medium, for example an inert solvent together with an excess of the aromatic compound and/or an excess of a strong proton acid.

When the reaction has reached substantial completion, which is typically indicated by the formation of a solution, the 4-hydroxybenzophenone product may be isolated from the reaction mixture and purified using conventional separation techniques, for example precipitation and filtration or distillation. When operated industrially, the separation methods employed will be such as to permit the maximum recovery and recycling of catalysts and solvents.

The method of the invention has been found to be particularly effective for the preparation of 4-fluoro-4'-hydroxybenzophenone by reacting poly(4-oxybenzoyl) with fluorobenzene, especially in the presence of acid catalysts such as trifluoromethanesulphonic acid or hydrogen fluoride/boron trifluoride. The desired product is obtained in very high purity accompanied by only small amounts (approximately 2%) of 2-fluoro-4'-hydroxybenzophenone. The high purity of the product makes it suitable for use as a polyetherketone precursor with little further purification.

Products such a 4 fluoro-4¹-hydroxybenzophenone may be used for the preparation of polyaryletherketones using a nucleophilic process, for example as described inter alia in British Pat. Nos. 1078234, and 1414421, Canadian Pat. No. 847963 and European Pat. No. 1879.

The invention is illustrated but not limited by the following Examples.

EXAMPLE 1

Fluorobenzene (5 cm³) and 3.6 g of commercial poly(4-oxybenzoyl) available from Carborundum Corporation under the trade mark "Ekonol", were added to trifluoromethanesulphonic acid (10 cm³) and the mixture was stirred under nitrogen for 16 hours at room temperature. The resulting suspension was poured into water, and the aqueous solution made alkaline by addition of solid sodium hydroxide. The unreacted polymer was filtered off, and the resulting clear yellow solution was acidified with hydrochloric acid, giving a white precipitate which was filtered off, washed with water, until the washings were acid-free and dried under vacuum at ambient temperature for 16 hours. This material weighed 1.9 g (24% yield based on polymer charged) and consisted essentially of 4-fluoro-4'-hydroxybenzophenone (98%) and 2-fluoro-4'-hydroxybenzophenone (2%).

The above procedure was repeated, but the poly(4-oxybenzoyl) was replaced by 3.6 g of 4-hydroxybenzoic acid. After the same reaction time, no fluorohydroxybenzophenone was obtained, only starting materials being isolated.

Poly(4-oxybenzoyl) is thus a more active hydroxybenzoylating agent under the conditions described than 4-hydroxybenzoic acid.

EXAMPLE 2

Finely divided poly(4-oxybenzoyl) available as 'Ekonol' (3.6 g, 30 mmol) and fluorobenzene (5 g, 53 mmol) were stirred in trifluoromethanesulphonic acid (10 cm$^3$) under nitrogen, and the mixture was heated to 80° C. After 2½ hours the suspension was cooled, poured into water (150 cm$^3$), and sodium hydroxide then added until the solution was alkaline. Hexane (100 cm$^3$) was added with vigorous stirring, and the aqueous phase was separated, filtered, and acidified with concentrated hydrochloric acid. The very pale, pink precipitate was filtered off, washed copiously with water to remove any 4-hydroxybenzoic acid, and was dried under vacuum at ambient temperature for 16 hours. The yield of hydroxyfluorobenzophenone, identified by i.r., n.m.r. and HPLC (High Pressure Liquid Chromatography), was 3.72 g (57%, based on polymer charged), and the product contained more than 97% of the 4,4'-isomer.

EXAMPLE 3

A mixture of fluorobenzene (12 g, 0.125 mol) and commercial poly(4-oxybenzoyl) (15 g, 0.125 mol) was heated in an autoclave with boron trifluoride (22 g, 0.323 mol) and hydrogen fluoride (40 g, 2 mol) at 100° C. for 5 hours. The reaction mixture was quenched in water and stirred for 3 hours. The red solid was filtered off, washed with water until the washings were acid-free and dried by passing air through the solid. The solid was then dissolved in 400 cm of 10% sodium hydroxide solution; this solution was filtered, and acidified with concentrated hydrochloric acid. The resulting pink precipitate was filtered off, washed with water until the washings were acid-free and dried to give 22.3 g of solid containing 98% of 4-fluoro-4'-hydroxybenzophenone. The yield was thus 81%.

EXAMPLE 4

A mixture of commercial poly(4-oxybenzoyl) (2.5 g, 0.021 mol) and diphenyl ether (1.7 g, 0.010 mol) was stirred, at ambient temperature, with trifluoromethanesulphonic acid (15 cm$^3$) under nitrogen. Stirring was continued for 15 hours. The resulting solution was poured into water (200 cm$^3$) at ambient temperature and the mixture was stirred. A white precipitate was formed which was filtered off and washed with water until the washings were acid-free. The solid was then dissolved in boiling ethanol, water was added to the boiling solution until a trace of precipitation was observed and the mixture was allowed to cool when the solid crystallized from the aqueous ethanol.

1.4 g of 4,4'-bis(4-hydroxybenzoyl)diphenyl ether was obtained. The product was identified by comparison of the H$^1$ nmr spectrum thereof with that of an authentic sample.

The procedure described was repeated using 4-hydroxybenzoic acid. The product obtained was 4-(4-hydroxybenzoyl)diphenyl ether, showing that only monosubstitution had occurred.

Poly(4-oxybenzoyl) is thus a more active hydroxybenzoylating agent than 4-hydroxybenzoic acid under the conditions used.

EXAMPLE 5

In this example, the poly(4-oxybenzoyl) was prepared from 4-hydroxybenzoic acid and this polymer was then used in place of the commercially available material used in the preceding examples.

4-hydroxybenzoic acid (20 g) was suspended in a mixture of trifluoroacetic anhydride and dichloromethane (100 cm$^3$). The mixture was stirred at ambient temperature under nitrogen for 12 hours. The product obtained (poly (4-oxybenzoyl)) was filtered off, washed with dichloromethane and dried under vacuum at room temperature for 16 hours.

4.8 g of the polymer thus obtained and 6 g of aluminium chloride were stirred in 40 cm$^3$ of fluorobenzene under nitrogen at 85° C. for three hours. After this time, essentially all of the polymer had dissolved, the mixture was cooled and poured into 200 cm$^3$ of stirred water at ambient temperature. A solid was precipitated. The mixture was made alkaline by the addition of 30% w/v or aqueous sodium hydroxide solution and the solid dissolved. The aqueous phase was separated and washed with 200 cm$^3$ of dichloromethane. Concentrated hydrochloric acid was then added to acidify the aqueous phase to pH 1 and cause the precipitation of 4-fluoro-4'-hydroxybenzophenone. The solid was filtered off, washed with water until the washings were acid-free and was then dried under vacuum at room temperature for 16 hours.

2.5 g of 4-fluoro-4'-hydroxybenzophenone of purity 95% was obtained. The yield was 30% based on the polymer.

We claim:

1. A process for the preparation of a 4-hydroxybenzophenone having the formula

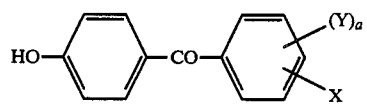

which comprises reacting a poly(4-oxybenzoyl) with an aromatic compound of the formula

in the presence of an effective amount of an acid catalyst, wherein
X represents hydrogen or a substituent that is not strongly electron-attracting;
Y is a substituent which is not strongly electron-attracting; and
a is zero or an integer of 1 to 4, the remaining substituents being hydrogen atoms and the overall effect of X and the substituents Y is not sufficient to deactivate the aromatic compound to such an extent that substitution occurs only with difficulty.

2. The process of claim 1 wherein, in the aromatic compound, X is an alkyl, an alkoxy, an aryl or an aryloxy group or a halogen atom.

3. The process of claim 1 wherein the acid catalyst is at least one of the group of strong proton acids and Lewis acids.

4. The process of claim 3 wherein the acid catalyst is hydrogen fluoride, a hydrogen fluoride/boron trifluoride mixture, trifluoromethanesulphonic acid or aluminium chloride.

5. The process of claim 1 which is effected at a temperature in the range from 20° C. to 150° C.

6. The process of claim 1 wherein at least one mole of the aromatic compound is used for each molecular equivalent of oxybenzoyl units present in the poly(4-oxybenzoyl).

7. The process of claim 1 wherein at least one equivalent of the acid catalyst is used for each molecular equivalent of oxybenzoyl units present in the poly(4-oxybenzoyl).

8. The process of claim 1 wherein an excess of the aromatic compound or an excess of a strong proton acid or an inert solvent is used as the reaction medium.

9. The process of claim 1 wherein 4-fluoro-4'-hydroxybenzophenone is obtained by reacting poly(4-oxybenzoyl) with fluorobenzene in the presence of trifluoromethanesulphonic acid or hydrogen fluoride/boron trifluoride.

10. A process of claim 1 wherein the poly(4-oxybenzoyl) has the formula

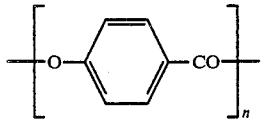

where n represents the degree of polymerization.

11. A process for the preparation of 4-hydroxybenzophenone having the formula:

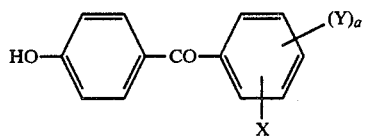

which comprises reacting a poly(4-oxybenzoyl) of the formula

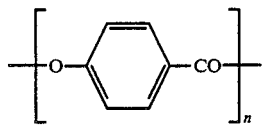

with an aromatic compound of the formula

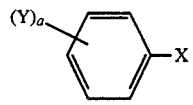

in the presence of an effective amount of an acid catalyst which is a strong proton acid, a Lewis acid or a mixture thereof, wherein X represents hydrogen or a substituent that is not strongly electron-attracting Y is a substituent that is not strongly electron-attracting;

a is zero or an integer of 1 to 4; and n represents the degree of polymerization and has a value in the range from 2 to 1000, the remaining substituents on the aromatic compound being hydrogen atoms and the overall effect of X and the substituents Y being insufficient to deactivate the aromatic compound to such an extent that substitution occurs only with difficulty and the aggregate of Hammett o constants of X and the substituents Y being less than 0.4.

* * * * *